United States Patent [19]

Wilk

[11] Patent Number: 5,312,391
[45] Date of Patent: May 17, 1994

[54] LAPAROSCOPIC INSTRUMENT ASSEMBLY

[76] Inventor: Peter J. Wilk, 185 W. End Ave., New York, N.Y. 10023

[21] Appl. No.: 922,165

[22] Filed: Jul. 29, 1992

[51] Int. Cl.⁵ .............................................. A61B 17/00
[52] U.S. Cl. ........................................ 606/1; 606/205; 604/264
[58] Field of Search .................. 606/1, 108, 110, 113, 606/114, 127, 170, 205–211, 39–42; 604/23, 26, 33, 95, 158, 264, 280, 281; 128/4, 6, 898

[56] References Cited

U.S. PATENT DOCUMENTS

| | | | |
|---|---|---|---|
| 3,834,392 | 9/1974 | Lampman et al. | 128/4 |
| 4,655,219 | 4/1987 | Petruzzi | 606/206 |
| 4,700,694 | 10/1987 | Shishido | 128/4 |
| 4,732,163 | 3/1988 | Bonello et al. | 604/280 |
| 4,924,851 | 5/1990 | Ognier et al. | 604/264 |
| 5,099,827 | 3/1992 | Melzer et al. | 128/4 |
| 5,144,942 | 9/1992 | Degrie et al. | 128/4 |

Primary Examiner—Stephen C. Pellegrino
Assistant Examiner—Glenn Dawson
Attorney, Agent, or Firm—R. Neil Sudol; Henry D. Coleman

[57] ABSTRACT

A laparoscopic instrument assembly includes a rigid sleeve and a plurality of laparoscopic instrument shafts inserted inside the sleeve. The sleeve has an outer diameter smaller than an inner diameter of a laparoscopic cannula, whereby a distal end portion of the instrument assembly may be inserted into a patient's abdomen through the laparoscopic cannula during a laparoscopic procedure. A plurality of surgical tips are operatively connected to respective ones of the shafts at distal ends thereof, while an actuator component is connected to the shafts at a proximal end of the sleeve for independently actuating the operative tips.

22 Claims, 2 Drawing Sheets

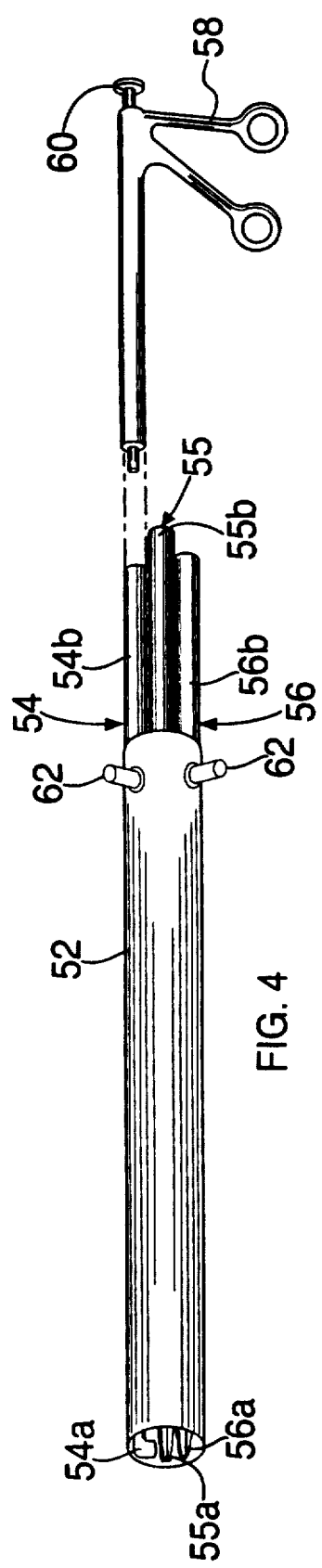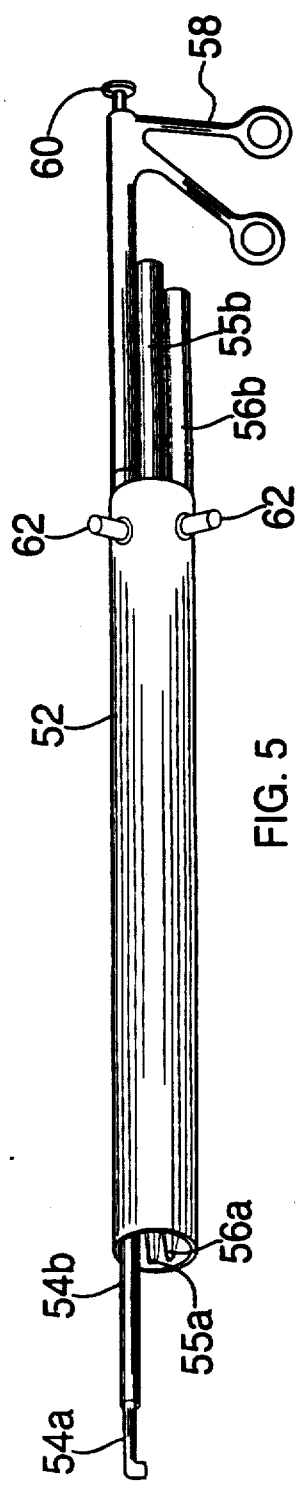

LAPAROSCOPIC INSTRUMENT ASSEMBLY

BACKGROUND OF THE INVENTION

This invention relates to a laparoscopic instrument assembly. This invention also relates to a method for use in laparoscopic surgery.

Laparoscopy involves the piercing of the abdominal wall and the insertion of a tubular port member or laparoscopic cannula through the perforation. Various instruments may be inserted through the tubular member to perform surgical operations inside the abdomen.

Generally, upon the disposition of the first cannula or trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Generally, laparoscopic surgery is performed with rigid instruments, the distal end portions of which are inserted into the patient's abdominal cavity through one or more tubular port members inserted in perforations formed in the abdominal wall. To enable the different laparoscopic surgical instruments to reach different locations within the abdominal cavity, the tubular cannulas are tilted or pivoted.

In a more recent development, the distal terminal portions of some laparoscopes are flexible and bendable under control of the surgeon by the manipulation of actuator members outside the patient. As in endoscopic surgery, surgical instruments such as biopsy forceps, graspers, trocars, suction devices, irrigators, scissors, cautery devices, staplers, suture applicators and clamps, may be inserted through one or more longitudinal channels in the laparoscopes or endoscopes. These instruments are at least partially flexible to enable them to flex with the bending type motions of the laparoscopes or endoscopes in which they are inserted.

It frequently occurs during laparoscopic surgery that an additional instrument is temporarily required. Inserting this extra instrument involves either temporarily removing one of the other instruments or forming another perforation with a trocar.

OBJECTS OF THE INVENTION

An object of the present invention is to provide a device and an associated method for facilitating laparoscopic surgery.

A more particular object of the present invention is to provide is to provide a laparoscopic instrument assembly and/or an associated method which provides an increased number of instruments without increasing the number of perforations in a patient's abdomen.

Another particular object of the present invention is to provide such an instrument assembly and or an associated surgical procedure which facilitates the performance of an operation by making a plurality of laparoscopic surgical instruments more readily manipulable by surgeon.

A further particular object of the present invention is to provide a method for the temporary provision of an extra laparoscopic instrument during laparoscopic surgery which does not require the formation of another perforation in the abdominal wall or the removal of another instrument from the abdomen.

These and other objects of the present invention will be apparent from the drawings and detailed descriptions herein.

SUMMARY OF THE INVENTION

A laparoscopic instrument assembly comprises, in accordance with the present invention, a rigid sleeve and a plurality of laparoscopic instrument shafts inserted inside the sleeve. The sleeve has an outer diameter smaller than an inner diameter of a laparoscopic cannula, whereby a distal end portion of the instrument assembly may be inserted into a patient's abdomen through the laparoscopic cannula during a laparoscopic procedure. A plurality of surgical tips are operatively connected to respective ones of the shafts at distal ends thereof, while an actuator component is connected to the shafts at a proximal end of the sleeve for independently actuating the operative tips.

An instrument assembly in accordance with the present invention enables the insertion of multiple laparoscopic instruments through a single trocar sleeve or laparoscopic cannula. Pursuant to one embodiment the present invention, the instruments are utilizable only in seriatum. Pursuant to another embodiment of the present invention, a plurality of the instruments may be used simultaneously. Generally, two instruments will be used by one surgeon.

According to another feature of the present invention, at least one of the shafts is slidably mounted to the sleeve for sliding motion relative thereto. Preferably, all of the shafts are slidably mounted to the sleeve for sliding motion relative thereto.

This slidability of the shaft or shafts relative to the sleeve enables an adjustment in the location of the operative tips of the instruments relative to a surgical site. For instance, one or more instruments may be withdrawn or retracted so that the respective operative tips are spaced from the surgical site. More particularly, one or more of the laparoscopic instruments of the assembly may be shifted in the proximal direction so that the respective operative tips are retracted inside the distal end of the sleeve, thereby ensuring that those operative tips are not exposed for possible inadvertant contact with internal organic tissues of the patient.

According to a further feature of the present invention, the instrument assembly further comprises a lock on the sleeve and the slidable instrument shaft or shafts for alternately locking that shaft in a retracted neutral position and an extended use position.

According to an additional feature of the present invention, at least one of the shafts is flexible in a distal end region. In that event, the instrument assembly further comprises a bend control operatively connected to the flexible shaft at a proximal end thereof for controlling the orientation of that shaft in its distal end region. Controlled flexibility of the distal ends of the laparoscopic instruments facilitates use of the instruments on the same surgical site. Thus, although all of the laparoscopic instruments project from approximately the same location at the distal end of a laparoscopic cannula or trocar sleeve through which the instrument assembly is inserted, one or more of the instruments may be operated to have a curved distal end, whereby the operative tip of the instrument approaches the surgical site at an angle relative to the laparoscopic cannula or trocar sleeve.

Pursuant to the one embodiment of the present invention, the actuator component is but a single actuator removably connected to one of the shafts, whereby the actuator may be transfered to another one of the shafts for actuating the respective operative tip thereof.

Pursuant to the other embodiment of the present invention, the actuator component is a plurality of separate actuators, one for each of the instrument shafts, whereby a plurality of the operative tips may be operated simultaneously from the proximal end of the sleeve.

Of course, the operative tips may have different structures, for performing different surgical operations.

A method for use in the performance of laparoscopic surgery comprises, in accordance with the present invention, the steps of (a) disposing a laparoscopic cannula in a patient's abdominal wall, (b) upon such disposition of the cannula, inserting through the cannula a rigid sleeve surrounding a plurality of laparoscopic instrument shafts, (c) initially manipulating an actuator at a proximal end of the sleeve to operate a surgical tip at a distal end of a first one of the shafts to perform a surgical operation, (d) subsequently manipulating an actuator at a proximal end of the sleeve to operate a surgical tip at a distal end of a second one of the shafts to perform another surgical operation, and (e) maintaining the sleeve in a position longitudinally traversing the cannula during the steps of manipulating.

Because the two surgical instruments protrude from the patient's abdomen at approximately the same location, namely, the proximal end of the particular laparoscopic cannula or trocar sleeve, the alternate or simultaneous handling of the instruments is facilitated. It is generally easier for a person to operate actuators which are closer to one another. In conventional laparoscopic surgery, two laparoscopic instruments are inserted through separate trocar sleeves which must necessarily be placed a minimal distance appart from one another.

Pursuant to another feature of the present invention, the method further comprises the step of sliding the one or the other of the instrument shafts relative to the sleeve prior to the manipulation of the respective instrument.

Prior to shifting or sliding of that shaft or instrument relative to the sleeve, the instrument is unlocked from the sleeve. Locking is desired to prevent inadvertant sliding of the instrument down into the abdominal cavity while another instrument or instruments are being used. In addition, an instrument shaft may be locked to the sleeve upon the attainment of a desired extended position of the intrument relative to the sleeve.

Where there is but one actuator at the proximal end of the instrument assembly, the surgical procedure includes the additional steps of removing the actuator from the proximal end of a first shaft upon manipulation of the respective laparoscopic instrument and connecting the removed actuator to the proximal end of a second shaft prior to the manipulation of the respective, second, instrument in a laparoscopic surgical procedure. The actuator is preferably locked to the successive shafts during use of the actuator to operate the respective laparoscopic instruments.

Alternatively, as described hereinabove with reference to the laparoscopic instrument assembly, there may be a plurality of actuators equal in number to and connected to the different instrument shafts. In this case, two laparoscopic instruments may be used by the same surgeon simultaneously.

Where an instrument shaft is flexible in a distal end region, the method further comprises the step of modifying the distal end orientation of that instrument shaft in the distal end region prior to the manipulation of the actuator at the proximal end of the respective instrument shaft.

A laparoscopic instrument assembly in accordance with the present invention and the associated method substantially facilitate laparoscopic surgery. An increased number of instruments is provided without increasing the number of perforations required in a patient,s abdomen. The performance of an operation is facilitated insofar as the actuators of a plurality of laparoscopic surgical instruments are closer to each other and therefore are more readily manipulable by surgeon. Moreover, the instant invention enables the temporary provision of an extra laparoscopic instrument during laparoscopic surgery which does not require the formation of another perforation in the abdominal wall or the removal of another instrument from the abdomen.

BRIEF DESCRIPTION OF THE DRAWING

FIG. 4 is an exploded schematic perspective view, on a reduced scale, of yet another laparoscopic instrument assembly in accordance with the present invention.

FIG. 5 is a schematic perspective view of the laparoscopic instrument assembly of FIG. 4, showing the assembly in one of several operational configurations.

DETAILED DESCRIPTION

Figure 1:
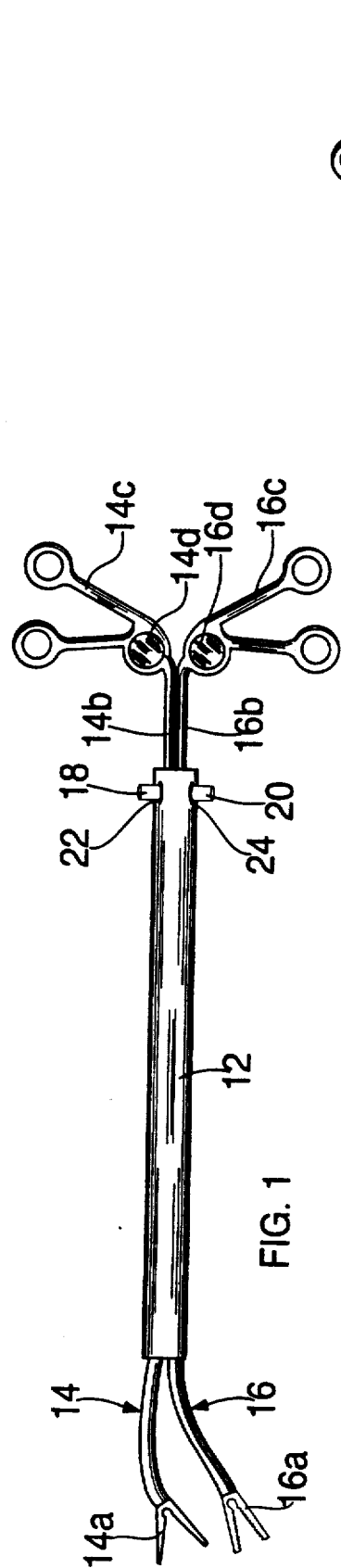
FIG. 1 is a schematic side elevational view, on a reduced scale, of a laparoscopic instrument assembly in accordance with the present invention, showing the assembly in one operational state.
Figure 2:
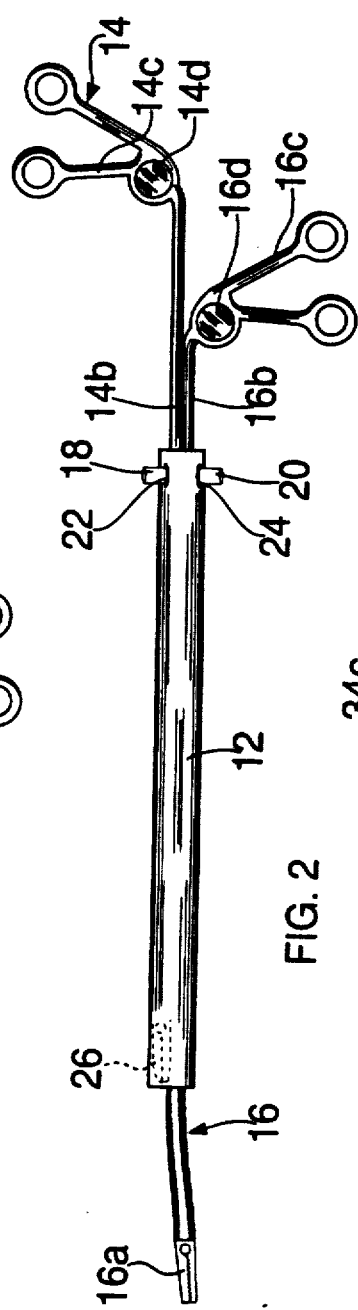
FIG. 2 is a schematic side elevational view of the laparoscopic instrument assembly of FIG. 1, showing the assmbly in a different operational state.

As illustrated in FIG. 1, a laparoscopic instrument assembly comprises a rigid sleeve 12 and a pair of lapároscopic instruments 14 and 16 inserted inside the sleeve. Each laparoscopic instrument 14 and 16 includes an operative tip 14a and 16a at a distal end, a shaft 14b and 16b, and an actuator 14c and 16c at a proximal end. Sleeve 12 has an outer diameter smaller than an inner diameter of a trocar sleeve or laparoscopic cannula (not shown), whereby a distal end portion of the instrument assembly may be inserted into a patient's abdomen through the laparoscopic cannula during a laparoscopic procedure. Laparoscopic instruments 14 and 16 may be used simultaneously (FIG. 1) or separately, in seriatum (FIG. 2).

Shafts 14b and 16b are slidably mounted to sleeve 12 for sliding motion relative thereto to enable adjustment in the location of the respective operative tips 14a and 16a relative to a surgical site. For instance, one or more instruments may be withdrawn or retracted so that the respective operative tips are spaced from the surgical site. More particularly, one or more of the laparoscopic instruments of the assembly may be shifted in the proximal direction so that the respective operative tips are retracted inside the distal end of the sleeve, thereby ensuring that those operative tips are not exposed for possible inadvertant contact with internal organic tissues of the patient.

Spring loaded locking pins 18 and 20 are provided on shafts 14b and 16b for cooperating with apertures 22 and 24 in sleeve 12 to alternately lock the respective shafts in a retracted neutral position and an extended use position. FIG. 1 shows both instruments 14 and 16 in an extended, use position relative to sleeve 12, while FIG. 2 shows instrument 14 shifted in a proximal direction relative to sleeve 12 to withdraw operative tip 14a into the distal end of sleeve 12, as indicated in dashed lines at 26. When both instruments 14 and 16 are being used, it may be desirable to lock only one of the instruments to sleeve 12 so that the instruments are slidable relative to one another, at least to a limited extent, for enhancing the modes of use of the instrument assembly.

Shafts 14b and 16b are flexible in a distal end region. Laparoscopic instruments 14 and 16 further comprise a bend control knob or knobs 14d and 16d operatively connected to the shafts 14b and 16b at a proximal end thereof for controlling the orientation of the respective shafts in their distal end regions. Ability to control the orientations of the distal ends of laparoscopic instruments 14 and 16 facilitates use of the instrument assembly of FIGS. 1 and 2. As depicted in FIG. 1, laparoscopic instruments 14 and 16 may be operated to have curved distal ends, whereby operative tip 14a and 16a approach a surgical site at respective angles relative to sleeve 12 and accordingly relative to a laparoscopic cannula through which the instrument assembly is inserted into a patient's abdomen.

As illustrated in FIG. 1, operative tips 14a and 16a are a scissors and a grasping forceps, respectively. However, it is to be noted that any combination of operative tips may be provided. Each operative tip 14a and 16a may be taken from the nonlimiting group including biopsy forceps, graspers, trocars, suction devices, irrigators, scissors, cautery devices, staplers, suture applicators and clamps.

In using the laparoscopic instrument assembly of FIGS. 1 and 2, a laparoscopic cannula is first inserted in a patient's abdominal wall by a conventional laparoscopic procedure. Upon such disposition of the cannula, distal end portion of the laparoscopic instrument assembly is inserted through the cannula so that sleeve 12, as well as shafts 14b and 16b longitudinally traverse the cannula. During insertion of the instrument assembly, the distal end portions of shafts 14b and 16b are maintained in a straightened configuration. In addition, the laparoscopic instruments 14 and 16 may be shifted so that operative tips 14a and 16a are retracted into the distal end of sleeve 12.

Upon insertion of the laparoscopic instrument assembly through the cannula so that the distal end of the assembly is disposed inside the patient's abdomen, the operator manipulates actuator 14c and/or 16c to operate the respective surgical tip 14a and/or 16a. Generally, one actuator 14c or 16c will be manipulated prior to the other, although eventually the operating surgeon will have a hand on each actuator 14c and 16c during a portion of a laparoscopic surgical procedure. If necessary, locking pin 18 and/or 20 is removed from aperture 22 and/or 24 prior to manipulation of actuator 14c and/or 16c to enable an adjustment of the position of the respective laparoscopic instrument 14 and/or 16 relative to sleeve 12. During the manipulation of actuators 14c and 16c, sleeve 12 is maintained in a position longitudinally traversing the laparoscopic cannula or trocar sleeve in the patient's abdominal wall.

Other locking pins (not illustrated) may be provided on laparoscopic instruments 14 and 16 and sleeve 12 for enabling the entrainment of the sleeve to one or more of the instrument shafts 14b or 16b during a laparoscopic surgical procedure. In particular, locking elements are advantageously provided for fixing each laparoscopic instrument 14 and 16 to sleeve 12 in the extended positions of the instruments illustrated in FIG. 1. It is to be noted that essentially any type of mechanism may be provided to lock laparoscopic instruments 14 and 16 to sleeve 12.

Because instrument shafts 14b and 16b are flexible at a distal end, the distal end orientations of shafts 14b and 16b may be adjusted via knobs 14d and 16d prior to the manipulation of the respective actuators 14c and 16c.

Figure 3:
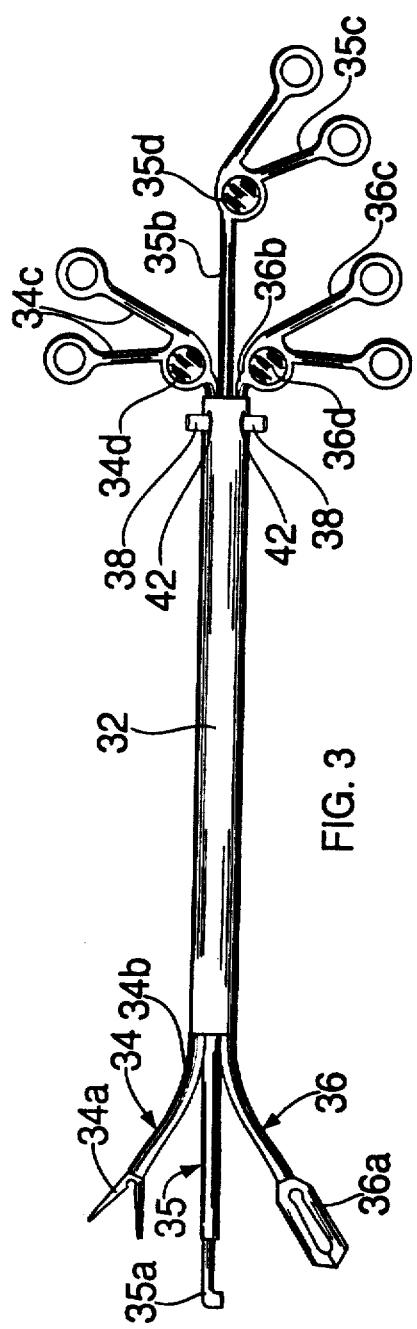
FIG. 3 is a schematic side elevational view, on a reduced scale, of another laparoscopic instrument assembly in accordance with the present invention.

As illustrated in FIG. 3, a modified laparoscopic instrument assembly comprises a rigid sleeve 32 and three laparoscopic instruments 34, 35, 36 inserted inside the sleeve. Each laparoscopic instrument 34, 35, 36 includes an operative tip 34a, 35a, 36a at a distal end, a central shaft 34b, 35b, 36b, and an actuator 34c, 35c, 36c at a proximal end. Sleeve 32 has an outer diameter smaller than an inner diameter of a trocar sleeve or laparoscopic cannula (not shown), whereby a distal end portion of the instrument assembly may be inserted into a patient's abdomen through the laparoscopic cannula during a laparoscopic procedure. Laparoscopic instruments 34, 35, 36 may be used simultaneously (FIG. 1) or separately, in seriatum (FIG. 2). Generally, one instrument 34, 35 or 36 is manipulated before the others at the onset of a laparoscopic surgical procedure, inasmuch as the surgeon's attention is directed to operating and placing the instruments in seriatum. In any event, at some time during the procedure, one actuator 34c, 35c or 36c will be manipulated and then subsequently a different actuator 34c, 35c or 36c will be operated. However, the surgeon may maintain his hands on two instruments during the entire procedure.

Shafts 34b, 35b, 36b are slidably mounted to sleeve 32 for sliding motion relative thereto to enable adjustment in the location of the respective operative tips 34a, 35a, 36a relative to a surgical site. For instance, one or more instruments 34, 35, 36 may be withdrawn or retracted so that the respective operative tips 34a, 35a, 36a are spaced from the surgical site. More particularly, one or more instruments 34, 35, 36 may be shifted in the proximal direction so that the respective operative tips 34a, 35a, 36a are retracted inside the distal end of sleeve 32, thereby ensuring that those operative tips are not exposed for possible inadvertant contact with internal organic tissues of the patient.

Spring loaded locking pins 38 are provided on shafts 34b, 35b, 36b for cooperating with apertures 42 in sleeve 32 to alternately lock the respective shafts in a retracted neutral position and an extended use position. Shafts 34b, 35b, 36b are flexible in a distal end region. Laparoscopic instruments 34, 35, 36 further comprise a bend control knob or knobs 34d, 35d, 36d operatively connected to the shafts 34b, 35b, 36b at a proximal end thereof for controlling the orientation of the respective shafts in their distal end regions. As depicted in FIG. 3, laparoscopic instruments 34, 35, 36 may be operated to have curved distal ends, whereby operative tip 34a, 35a, 36a approach a surgical site at respective angles relative to sleeve 32 and accordingly relative to a laparoscopic cannula through which the instrument assembly is inserted into a patient's abdomen.

As illustrated in FIG. 3, operative tips 34a, 35a, 36a are a scissors, a hook and a clamping forceps, respectively. However, it is to be noted that any combination of operative tips may be provided. Each operative tip 34a, 35a, 36a may be taken from the non-limiting group including biopsy forceps, graspers, trocars, suction devices, irrigators, scissors, cautery devices, staplers, suture applicators and clamps.

The operation of the laparoscopic instrument assembly of FIG. 3 is essentially the same as the operation of the instrument assembly of FIGS. 1 and 2. It is to be noted that on instrument 34, 35, 36 may remain in place without manipulation of the respective actuator 34c, 35c, 36c. For example, clamping forceps 36c may remain attached to an organ while the surgeon is manipulating actuators 35c and 36c to control the operation of scissors 34a and hook 35a. Alternatively, a non-used instrument 34, 35, 36 may be retracted to a storage position inside sleeve 32.

As illustrated in FIGS. 4 and 5, another laparoscopic instrument assembly comprises a rigid sleeve 52 and a plurality of laparoscopic instrument shafts 54b, 55b, 56b inserted inside sleeve 52. Sleeve 52 has an outer diameter smaller than an inner diameter of a laparoscopic cannula, whereby a distal end portion of the instrument assembly may be inserted into a patient's abdomen through the laparoscopic cannula during a laparoscopic procedure. A hook 54a, a scissors 55a, and a grasping forceps 56a are operatively connected to respective shafts 54b, 55b, 56b at distal ends thereof, while an actuator component 58 is removably connectable successively to the different shafts 54b, 55b, 56b at a proximal end of sleeve 52 for independently actuating operative tips 54a, 55a, 56a.

Shafts 54b, 55b, 56b are slidably mounted to sleeve 52 for shifting instruments 54, 55, 56 between a retracted or storage position (FIG. 4) and an extended or use position (see instrument 54 in FIG. 5). In a preferred method of using the instrument assembly of FIGS. 4 and 5, only one instrument 54, 55, 56 at a time is shifted into the extended or use position, as shown in FIG. 5. However, particularly if shafts 54b, 55b, 56b are provided with controllably flexible distal end portions, it may be possible to operate one instrument 54, 55, 56 while another is extended. For example, grasping forceps 56a may be left grasping internal tissues of a patient while actuator component or handle 58 is removed from shaft 56b and connected to the proximal end of shaft 55b for manipulating scissors 55a.

Prior to the extension of the respective instrument, for example, instrument 54, actuator component or handle 58 is attached to the proximal end of instrument shaft 54b, as shown in FIG. 5. Actuator component 58 is provided with a latch or detent 60 for locking the actuator component to any one of the shafts 54b, 55b, 56b.

In using the instrument assembly of FIGS. 4 and 5, multiple laparoscopic instruments 54, 55, 56 are simultaneously inserted through a single trocar sleeve or laparoscopic cannula. To change from one instrument 54, 55, 56 to another, the surgeon simply disconnects actuator component or handle 58 from the shaft 54b, 55b, 56b of one instrument 54, 55, 56 and connects it to the shaft of another instrument. Of course, the first instrument may be retracted into sleeve 52 prior to the extension of the other.

Locking pins 62 may be provided for alternately locking shafts 54b, 55b, 56b in a retracted neutral position and an extended use position.

Of course, the operative tips 54a, 55a, 56a may have different structures, for performing different surgical operations.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A laparoscopic instrument assembly comprising:
   a rigid sleeve having an outer diameter smaller than an inner diameter of a laparoscopic cannula, whereby a distal end portion of the instrument assembly may be inserted into a patient's abdomen through the laparoscopic cannula during a laparoscopic procedure;
   a plurality of laparoscopic instrument shafts inserted inside said sleeve, at least one of said shafts being slidably mounted to said sleeve for sliding motion relative thereto;
   locking means on said sleeve and said one of said shafts for alternately locking said one of said shafts in a retracted neutral position and an extended use position;
   a plurality of surgical tips operatively connected to respective ones of said shafts at distal ends thereof; and
   actuator means connected to at least a given one of said shafts at a proximal end of said sleeve for actuating a respective one of said surgical tips.

2. The assembly defined in claim 1 wherein all of said shafts are slidably mounted to said sleeve for sliding motion relative thereto.

3. The assembly defined in claim 1 wherein at least one of said shafts is flexible in a distal end region, further comprising bend control means operatively connected to said one of said shafts at a proximal end for controlling the orientation of said one of said shafts in said distal end region.

4. The assembly defined in claim 1 wherein said actuator means includes a separate actuator for each of said shafts, whereby a plurality of said surgical tips may be operated simultaneously from said proximal end of said sleeve.

5. The assembly defined in claim 1 wherein said surgical tips have different structures, for performing different surgical operations.

6. The assembly defined in claim 1 wherein said actuator means includes a single actuator removably connected to said given one of said shafts, whereby said actuator may be transfered to another one of said shafts for actuating the respective surgical tip thereof.

7. A laparoscopic instrument assembly comprising:
   a rigid sleeve having an outer diameter smaller than an inner diameter of a laparoscopic cannula, whereby a distal end portion of the instrument assembly may be inserted into a patient's abdomen through the laparoscopic cannula during a laparoscopic procedure;

a plurality of laparoscopic instrument shafts inserted inside said sleeve, at least one of said shafts being flexible in a distal end region;

locking means on said sleeve for releasably locking at least one of said shafts to said sleeve;

a plurality of surgical tips operatively connected to respective ones of said shafts at distal ends thereof;

manual actuator means connected to each of said shafts at a proximal end thereof for independently actuating respective ones of said surgical tips; and bend control means operatively connected to said one of said shafts at a proximal end for controlling the orientation of said one of said shafts in said distal end region.

8. The assembly defined in claim 7 wherein at least said one of said shafts is slidably mounted to said sleeve.

9. The assembly defined in claim 8 wherein said locking means is adapted for alternately locking said one of said shafts in a retracted neutral position and an extended use position.

10. The assembly defined in claim 7 wherein said surgical tips have different structures, for performing different surgical operations.

11. A laparoscopic instrument assembly comprising:
a rigid sleeve having an outer diameter smaller than an inner diameter of a laparoscopic cannula, whereby a distal end portion of the instrument assembly may be inserted into a patient's abdomen through the laparoscopic cannula during a laparoscopic procedure;

a plurality of laparoscopic instrument shafts slidably inserted inside said sleeve;

a plurality of surgical tips operatively connected to respective ones of one said shafts at distal ends thereof; and actuator means connected to one said shafts at a proximal end of said sleeve for actuating a respective one of said surgical tips, said actuator means being removably connected to said one of said shafts, whereby said actuator means may be transfered to another one of said shafts to actuate a different one of said surgical tips.

12. The assembly defined in claim 11, further comprising locking means on said sleeve and said one of said shafts for alternately locking said one of said shafts in a retracted neutral position and an extended use position.

13. The assembly defined in claim 11 wherein said surgical tips have different structures, for performing different surgical operations.

14. A method for use in the performance of laparoscopic surgery, comprising the steps of:
providing a laparoscopic instrument assembly including a rigid sleeve surrounding a plurality of laparoscopic instrument shafts each having a surgical tip at a distal end, a first one of said shafts being slidably mounted to said sleeve, said first one of said shafts being locked to said sleeve;

disposing a laparoscopic cannula in a patient's abdominal wall;

upon such disposition of said cannula, inserting said instrument assembly through said cannula;

unlocking said first one of said shafts from said sleeve;

upon unlocking of said first one of said shafts from said sleeve, sliding said first one of said shafts relative to said sleeve;

upon sliding of said first one of said shafts relative to said sleeve, locking said first one of said shafts to said sleeve;

upon locking of said first one of said shafts to said sleeve, initially manipulating an actuator at a proximal end of said first one of said shafts to operate a surgical tip at a distal end of said first one of said shafts to perform a surgical operation;

subsequently manipulating an actuator at a proximal end of a second one of said shafts to operate a surgical tip at a distal end of said second one of said shafts to perform another surgical operation; and maintaining said sleeve in a position longitudinally traversing said cannula during said steps of manipulating.

15. The method defined in claim 14 wherein said second one of said shafts is slidably mounted to said sleeve, further comprising the step of sliding said second one of said shafts relative to said sleeve prior to said step of subsequently manipulating.

16. The method defined in claim 15 wherein said second one of said shafts is locked to said sleeve prior to said step of inserting, further comprising the step of unlocking said second one of said shafts from said sleeve prior to said step of sliding said second one of said shafts, also comprising the step of locking said second one of said shafts to said sleeve upon completion of said step of sliding said second one of said shaft.

17. The method defined in claim 14 wherein the actuator at the proximal end of said first one of said shafts is different from the actuator at the proximal end of said second one of said shafts.

18. The method defined in claim 14 wherein said first one of said shafts has a distal end region and is flexible in said distal end region, further comprising the step of modifying a distal end orientation of said first one of said shafts in said distal end region prior to said step of initially manipulating.

19. The method defined in claim 14 wherein said second one of said shafts has a distal end region and is flexible in said distal end region, further comprising the step of modifying a distal end orientation of said second one of said shafts in said distal end region prior to said step of subsequently manipulating.

20. The method defined in claim 16 wherein said surgical tips have different structures, for performing different surgical operations.

21. A method for use in the performance of laparoscopic surgery, comprising the steps of:
providing a laparoscopic instrument assembly including a rigid sleeve surrounding a plurality of laparoscopic instrument shafts each having a surgical tip at a distal end;

disposing a laparoscopic cannula in a patient's abdominal wall;

upon such disposition of said cannula, inserting said instrument assembly through said cannula;

initially manipulating an actuator at a proximal end of a first one of said shafts to operate a surgical tip at a distal end of said first one of said shafts to perform a surgical operation;

subsequently manipulating an actuator at a proximal end of a second one of said shafts to operate a surgical tip at a distal end of said second one of said shafts to perform another surgical operation, the actuator at the proximal end of said first one of said shafts being the same as the actuator at the proximal end of said second one of said shafts;

removing the actuator from the proximal end of said first one of said shafts upon completion of said step of initially manipulating and connecting the removed actuator to the proximal end of said second one of said shafts prior to said step of subsequently manipulating; and maintaining said sleeve in a position longitudinally traversing said cannula during said steps of manipulating.

22. The method defined in claim 21 wherein the actuator is locked to said first one of said shafts prior to said step of inserting, further comprising the steps of unlocking the actuator from said first one of said shafts prior to said step of removing, also comprising the step of locking the actuator to said second one of said shafts upon completion of said step of connecting.

* * * * *

UNITED STATES PATENT AND TRADEMARK OFFICE
CERTIFICATE OF CORRECTION

PATENT NO. : 5,312,391

DATED : May 17, 1994

INVENTOR(S) : Peter J. Wilk

It is certified that error appears in the above-indentified patent and that said Letters Patent is hereby corrected as shown below:

Column 1, line 63, delete "is to provide".

Column 2, line 32, insert --of-- after "embodiment".

Column 3, line 47, change "appart" to --apart--; line 60, change "intrument" to --instrument--.

Column 4, line 21, change "patient,s" to --patient's--; line 24, insert --a-- after "by"; line 39, change "assmbly" to --assembly--.

Column 5, line 50, insert --the-- after "cannula,".

Column 7, line 19, delete "on"; line 21, change "36c" to --36a--; line 23, change "35c and 36c" to --34c and 35c--.

Column 8, line 50, after "said" (first occurrence), insert --selected--.

UNITED STATES PATENT AND TRADEMARK OFFICE
CERTIFICATE OF CORRECTION

PATENT NO. : 5,312,391
DATED : May 17, 1994
INVENTOR(S) : Peter J. Wilk

Page 2 of 2

It is certified that error appears in the above-indentified patent and that said Letters Patent is hereby corrected as shown below:

Column 8, line 47 (claim 3), insert --a selected-- after "least"; line 51 (claim 3), insert --selected-- after "said" (first occurrence).

Column 9, line 39 (claim 11), delete "one".

Column 10, line 31 (claim 16), change "shaft" to --shafts--.

Signed and Sealed this

Fourteenth Day of March, 1995

BRUCE LEHMAN

Attest:

Attesting Officer

Commissioner of Patents and Trademarks